(12) United States Patent
Okada et al.

(10) Patent No.: US 8,148,574 B2
(45) Date of Patent: Apr. 3, 2012

(54) METHOD FOR PRODUCING 5-AMINOLEVULINIC ACID HYDROCHLORIDE

(75) Inventors: Hideki Okada, Saitama (JP); Tohru Tanaka, Tokyo (JP); Takeshi Nomura, Tokyo (JP)

(73) Assignee: Cosmo Oil Co., Ltd., Tokyo (JP)

( * ) Notice: Subject to any disclaimer, the term of this patent is extended or adjusted under 35 U.S.C. 154(b) by 688 days.

(21) Appl. No.: 12/063,883

(22) PCT Filed: Sep. 5, 2006

(86) PCT No.: PCT/JP2006/317570
§ 371 (c)(1),
(2), (4) Date: Mar. 19, 2008

(87) PCT Pub. No.: WO2007/034673
PCT Pub. Date: Mar. 29, 2007

(65) Prior Publication Data
US 2009/0036709 A1 Feb. 5, 2009

(30) Foreign Application Priority Data

Sep. 21, 2005 (JP) ................ P2005-273398

(51) Int. Cl.
*C07C 227/00* (2006.01)
*C07C 229/00* (2006.01)
(52) U.S. Cl. ........................... 562/554; 562/567
(58) Field of Classification Search .............. None
See application file for complete search history.

(56) References Cited

U.S. PATENT DOCUMENTS

| 3,221,008 A | * | 11/1965 | Wolf et al. ............... 536/13 |
| 3,846,490 A | * | 11/1974 | Aronova et al. ........... 562/567 |
| 4,733,009 A |   | 3/1988  | Miyahara et al. |
| 2007/0203027 A1 | * | 8/2007 | Tachiya et al. ............ 504/194 |

FOREIGN PATENT DOCUMENTS

| JP | 48-92328 A | 11/1973 |
| JP | 60-139656 A | 7/1985 |
| JP | 62-111953 A | 5/1987 |
| JP | 62-111954 A | 5/1987 |
| JP | 1-148193 A | 6/1989 |
| JP | 2-67256 A | 3/1990 |
| JP | 2-76841 A | 3/1990 |
| JP | 2-261389 A | 10/1990 |
| JP | 5-184376 A | 7/1993 |
| JP | 6-172281 A | 6/1994 |
| JP | 6-277081 A | 10/1994 |
| JP | 7-188133 A | 7/1995 |
| JP | 9-316041 A | 12/1997 |
| JP | 11-42083 A | 2/1999 |
| KR | 10-2005-0051612 A | 6/2005 |
| WO | 2005/100300 A1 | 10/2005 |
| WO | WO 2005/100300 | * 10/2005 |

OTHER PUBLICATIONS

Weiss, Handbook of Ion Chromatography, Third, Completely Revised and Enlarged Edition, 2004, Wiley-VCH Verlag GmbH & Co, Weinheim, Germany, pp. 1-11.*
Elliot, Biochemical Journal, Estimation of Aminoacetone and delta-Aminolaevulinic Acid, 1960, 74, pp. 90-94.*
Chen et al, Analytica Chemica Acta, Liquid Chromatography of Carboxylic Acids Using Potentiometric Detection With a Tungsten Oxide Electrode, 1997, 338, pp. 41-49.*
Di Venosa, G., "A method for separating ALA from ALA derivatives using ionic exchange extraction", Journal of Photochemistry and Photobiology, 2004, pp. 157-163, Elsevier Science, XP 004549147.
Extended European Search Report issued in European Application No. 06797470.9 dated Mar. 15, 2010.
"Atarashii Ekitai Chromatography" edited by Hiroyuki Hatano, Nankodo Co., Ltd., 3rd edition Hakko, Mar. 10, 1976, pp. 24-37.
'Kagaku No Ryoiki Zokan 109 Go', Oyo Kosoku Ekitai Chromatography, edited by Hiroyuki Hatano, Nankodo Co., Ltd., Mar. 31, 1976, pp. 43-49.
Communication dated Dec. 22, 2010, issued in corresponding Chinese Patent Application No. 200680034472.2.
Japanese Office Action, dated Apr. 12, 2011, issued in Application No. 2005-273398.
Australian Office Action dated May 27, 2011 issued in corresponding Australia Application No. 2006293300.
European Office Action issued in corresponding European Application No. 06797470.9 on Jun. 1, 2011.
European Office Action dated Nov. 29, 2011 issued by the European Patent Office in corresponding European Application No. 06797470.9.
European Search Report dated Dec. 2, 2011 issued by the European Patent Office in corresponding European Application No. 11183090.7.
Japanese Decision for Rejection issued Dec. 6, 2011 by the Japanese Patent Office in corresponding Japanese Application No. 2005-273398.

* cited by examiner

*Primary Examiner* — Paul A Zucker
(74) *Attorney, Agent, or Firm* — Sughrue Mion, PLLC

(57) ABSTRACT

A method for producing crystals of 5-aminolevulinic acid hydrochloride wherein, in carrying out adsorption of 5-aminolevulinic acid contained in a crude 5-aminolevulinic acid solution by a cation exchange resin and its subsequent desorption with an aqueous solution containing ammonium ion, a high purity 5-aminolevulinic acid aqueous solution is obtained using a change in electric conductivity or pH of the desorption liquid as the index, and chloride ion is added to the aqueous solution which is then mixed with an organic solvent.

13 Claims, 3 Drawing Sheets

METHOD FOR PRODUCING 5-AMINOLEVULINIC ACID HYDROCHLORIDE

TECHNICAL FIELD

This invention relates to a method for producing 5-aminolevulinic acid aqueous solution and 5-aminolevulinic acid hydrochloride which are useful in the fields of microorganisms and fermentations, animals and medical treatments, plants and the like.

BACKGROUND OF THE INVENTION

It is known that 5-aminolevulinic acid is useful in the field of microorganisms for vitamin $B_{12}$ production, heme enzyme production, microbial culturing, porphyrin production and the like, in the field of animals and the field of medical treatment for infectious disease treatment, sterilization, Haemophilus diagnosis, derivatives material, depilation, rheumatism therapy, cancer therapy, thrombus therapy, intraoperative diagnosis of cancer, animal cell culturing, heme metabolism studies, hair growth tonic, diagnosis of heavy metal intoxication porphyria, prevention of anemia and the like, and in the field of agriculture for plant growth regulation, salt resistance and the like.

On the other hand, production methods of 5-aminolevulinic acid are roughly classified into chemical synthesis and microbial fermentation. Regarding the chemical synthesis, methods have been reported which use, as the materials, hippuric acid (cf. Patent Reference 1), succinic acid monoester chloride (cf. Patent Reference 2), furfurylamine (e.g., see Patent Reference 3), hydroxymethylfurfural (cf. Patent Reference 4), oxovaleric acid methyl ester (cf. Patent Reference 5) and succinic acid anhydride (cf. Patent Reference 6). Regarding the microbial fermentation, methods which use anaerobic microbes, algae, photosynthetic bacteria, various recombinant microbes and the like have been reported. Particularly, a fermentation method by using a photosynthetic bacterium belonging to the genus *Rhodobacter* is typical (cf. Patent Reference 7).

However, there are cases in which the 5-aminolevulinic acid crude solutions produced by the aforementioned methods are used by purifying them in response to the purposes. The microbial fermentation method is known as an inexpensive industrial production method of 5-aminolevulinic acid, but saccharides, protein, amino acids, organic acids, metal ions and the like various compounds coexist in the culture. Particularly, glycine and the like amino acids whose chemical properties are close to those of 5-aminolevulinic acid are difficult to remove from the 5-aminolevulinic acid crude solution. In addition, in producing crystals of 5-aminolevulinic acid hydrochloride, it is crystallized by mixing a 5-amino levulinic acid hydrochloride aqueous solution with a poor solvent, but this crystallization step has a problem in that when glycine and the like amino acids and other contaminants are present, they inhibit the crystallization of 5-aminolevulinic acid hydrochloride. Accordingly, it is necessary to remove these contaminants before the crystallization step.

On the other hand, salts of 5-aminolevulinic acid have markedly high water-solubility, and the solubility in the case of 5-aminolevulinic acid hydrochloride is 3 M or more at room temperature, though it depends on the pH and temperature of the aqueous solution, solute coexisting in the aqueous solution and the like. Thus, it is desirable that the aqueous solution of 5-aminolevulinic acid hydrochloride to be used in the crystallization step is highly concentrated to a level close to its saturation solubility. As described in the foregoing, in order to produce crystals of 5-aminolevulinic acid hydrochloride, it is necessary to remove impurities which prevent crystallization and also to concentrate 5-aminolevulinic acid hydrochloride by dehydration. A vacuum concentrator can be exemplified as such a dehydration concentration technique, but in the case of the concentration of a large volume of a 5-aminolevulinic acid hydrochloride aqueous solution for its industrial production, it is necessary to heat the 5-aminolevulinic acid hydrochloride aqueous solution for a long time under the low pressure, so that operation of the apparatus requires large calories accompanied by the heating and cooling. In addition, since chloride ions are contained in the 5-aminolevulinic acid hydrochloride, it is necessary to take into consideration not only pressure resistance property of the vacuum concentrator but also its corrosion resistance. Accordingly, a technique for the dehydration concentration of aqueous solution of 5-aminolevulinic acid hydrochloride, which is different from the vacuum concentration have been desired.

Patent Reference 1: JP-A-48-92328
Patent Reference 2: JP-A-62-111954
Patent Reference 3: JP-A-2-76841
Patent Reference 4: JP-A-6-172281
Patent Reference 5: JP-A-7-188133
Patent Reference 6: JP-A-9-316041
Patent Reference 7: JP-A-11-42083

DISCLOSURE OF THE INVENTION

Problems that the Invention is to Solve

Accordingly, the invention is to provide methods for producing 5-aminolevulinic acid aqueous solution and 5-aminolevulinic acid hydrochloride by specifically separating 5-aminolevulinic acid from a crude 5-aminolevulinic acid solution.

Means for Solving the Problems

As a result of carrying out intensive studies, the present inventors have found that a 5-aminolevulinic acid aqueous solution in which 5-aminolevulinic acid is concentrated by removing contaminants to a practically acceptable degree for crystallization and so on, by using a change in electric conductivity or pH of the desorption liquid as the index of its recovery, after allowing 5-aminolevulinic acid contained in a 5-aminolevulinic acid crude solution to adsorb to a cation exchange resin and at the time of carrying out its desorption with an aqueous solution containing a cation. In addition, it was found that crystals of 5-aminolevulinic acid hydrochloride can be obtained by mixing the desorption liquid with chloride ion and mixing with an organic solvent, thereby accomplishing the invention.

That is, the invention provides a method for producing a 5-aminolevulinic acid aqueous solution, characterized in that a crude 5-aminolevulinic acid solution is allowed to contact with a cation exchange resin to effect adsorption of 5-aminolevulinic acid in the solution into the cation exchange resin, 5-aminolevulinic acid is desorbed from the cation exchange resin with an aqueous solution containing a cation to obtain a desorption liquid, and 5-aminolevulinic acid is recovered using a change in electric conductivity or pH of the desorption liquid as the index.

Also, the invention provides a method for producing 5-aminolevulinic acid hydrochloride, characterized in that the 5-aminolevulinic acid aqueous solution obtained in the above is allowed to contact with chloride ion.

In addition, the invention provides a method for producing crystals of 5-amino levulinic acid hydrochloride, characterized in that the 5-aminolevulinic acid aqueous solution obtained in the above is allowed to contact with chloride ion, and the thus obtained solution is mixed with at least 1 organic solvent of alcohols or ketones.

Advantage of the Invention

According to the invention, high purity 5-aminolevulinic acid aqueous solution and 5-aminolevulinic acid hydrochloride can be produced.

BEST MODE FOR CARRYING OUT THE INVENTION

Figure 1:
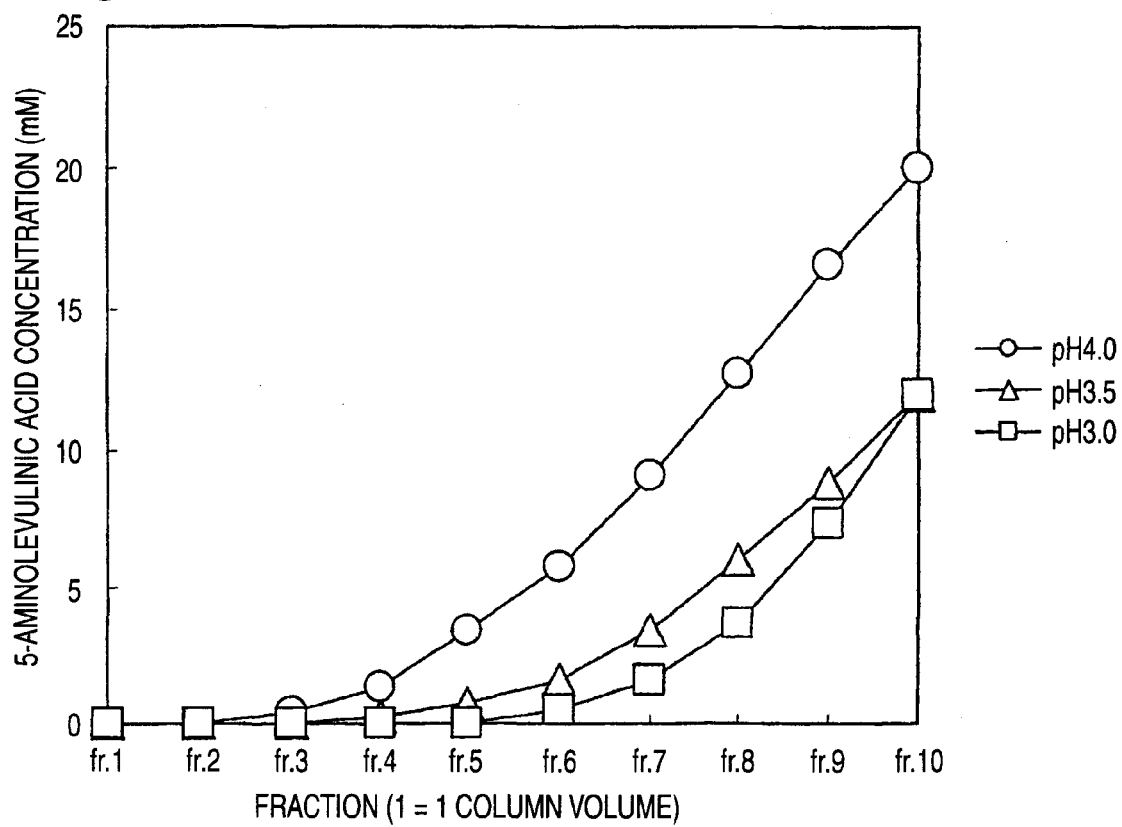
FIG. 1 is a graph showing a relationship between the pH of a crude aqueous solution containing 5-aminolevulinic acid and the 5-aminolevulinic acid concentration of a column passed-through liquid in column adsorption of 5-aminolevulinic acid.

Regarding the 5-aminolevulinic acid crude solution to be used in producing the 5-aminolevulinic acid aqueous solution and 5-aminolevulinic acid hydrochloride of the invention, it is not particularly limited with the proviso that it is a crude solution in which 5-aminolevulinic acid is dissolved in a solvent, and its purity and the like are not limited too. That is, 5-aminolevulinic acid crude solutions produced by chemical synthesis or microbial fermentation in accordance with the methods described in JP-A-48-92328, JP-A-62-111954, JP-A-2-76841, JP-A-6-172281, JP-A-7-188133, JP-A-11-42083 and the like, and the chemical synthesis solutions and fermentation liquids before their purification, can be used. The concentration of 5-aminolevulinic acid in these solutions is preferably 0.1 mM or more, more preferably from 0.1 mM to 3 M, particularly preferably from 1 mM to 3 M.

There are cases in which saccharides, amino acids, organic acids, alcohols, metal ion, protein, boric acid, phosphoric acid and the like are contained in the 5-aminolevulinic acid crude solutions produced by the chemical synthesis or microbial fermentation method described in the aforementioned official gazettes and the like, and particularly, there is a case in which glycine coexists therewith in the case of a 5-aminolevulinic acid crude solution produced by a fermentation method.

Adsorption of 5-aminolevulinic acid by a cation exchange resin can be carried out by allowing a 5-aminolevulinic acid crude solution to contact with the cation exchange resin. The solvent of 5-aminolevulinic acid crude solution is not particularly limited with the proviso that 5-aminolevulinic acid dissolves therein, and its examples include water, dimethyl sulfoxide, alcohols (methanol, ethanol, propanol, isopropanol, butanol, isobutanol and the like), amides (N,N-dimethylformamide, N,N-dimethylacetamide and the like), pyridines and the like, of which water, dimethyl sulfoxide, methanol and ethanol are desirable and water is particularly desirable, or two or more solvents may be used as a mixture.

The pH of 5-aminolevulinic acid crude solution is not particularly limited, but it is desirable that the pH is from 0.5 to 7, and it is particularly desirable that the pH is from 2.5 to 5. As the pH adjusting agent for adjusting this pH, hydrochloric acid, sulfuric acid, sulfurous acid, phosphoric acid, phosphorous acid, nitric acid, nitrous acid, boric acid, organic acids (phthalic acid, citric acid, succinic acid, acetic acid, lactic acid, tartaric acid, oxalic acid, phthalic acid, maleic acid and the like), Tris, MOPS, potassium hydroxide, sodium hydroxide, sodium carbonate, potassium carbonate, ammonia and the like can be exemplified, and two or more of them may be used as a mixture. As the cation exchange resin, it may be either a strong acid cation exchange resin or a weak acid cation exchange resin. Among them, a strong acid cation exchange resin is desirable. Regarding the species of the strong acid cation exchange resin, a strong acid cation exchange resin of a polystyrene type resin in which the functional group is sulfonate group is particularly desirable. As the ion binding to the functional group, hydrogen ion or ammonium ion is desirable.

The cation-containing aqueous solution to be used for the desorption is not particularly limited, but those in which phosphoric acid, hydroxide of an alkali metal or alkaline earth metal or a compound having carbonate, ammonia, amine or amino group is dissolved in water are desirable. Illustratively, those in which lithium hydroxide, sodium hydroxide, magnesium hydroxide, potassium hydroxide, calcium hydroxide, cesium hydroxide, barium hydroxide, ammonium carbonate, ammonium hydrogencarbonate, sodium carbonate, sodium bicarbonate, potassium carbonate, potassium sodium carbonate, potassium bicarbonate, ammonia, methylamine, dimethylamine, trimethylamine, ethylamine, diethylamine or triethylamine is dissolved in water are desirable, and those in which ammonia is dissolved in water are particularly desirable. These aqueous solutions may be used as a combination of two or more species. Concentration of the aqueous ammonia is preferably from 0.01 to 10 M, more preferably from 0.1 to 3 M, particularly preferably from 0.1 to 2 M.

Regarding the method for recovering the 5-aminolevulinic acid desorbed from the cation exchange resin, a change in pH or electric conductivity of the 5-aminolevulinic acid desorption liquid can be used as the index. Such a change is defined as the rate of change per column volume, and hereinafter called rate of change in electric conductivity or rate of change in pH.

When the desorption liquid is passed through a column which adsorbed 5-aminolevulinic acid under stationary state of washing with water, start of the desorption of 5-aminolevulinic acid is shown by the increase of electric conductivity or the increase of pH to around neutral pH.

When the rate of change in electric conductivity shows 0.1 mS/cm/column volume or more, or the rate of change in pH 0.1/column volume or more, it can be used as the index of the recovery commencement of the 5-aminolevulinic acid aqueous solution. More preferably, a rate of change in electric conductivity of 0.5 mS/cm/column volume or more, or a rate of change in pH of 0.5/column volume or more, can be used as the index.

Thereafter, the electric conductivity or pH slowly increases proportional to the increase of 5-aminolevulinic acid concentration, and their rates of change are reduced, and 5-aminolevulinic acid can be recovered while confirming this change.

In addition, completion of desorption of 5-aminolevulinic acid is shown by rapid increase of electric conductivity or rapid increase of pH in the 5-aminolevulinic acid recovery liquid. When the rate of change in electric conductivity shows 2.5 mS/cm/column volume or more, or the rate of change in pH 0.6/column volume or more, it can be used as the index of the recovery completion of the 5-aminolevulinic acid aqueous solution. More preferably, a rate of change in electric conductivity of 7 mS/cm/column volume or more, or a rate of change in pH of 1/column volume or more, can be used as the index.

5-Aminolevulinic acid can be recovered using a combination of these indexes of recovery commencement and recovery completion of the 5-aminolevulinic acid aqueous solution, and it is desirable to use the rate of change in electric conductivity as the index at the time of recovery commencement of 5-aminolevulinic acid, and the rate of change in pH as the index at the time of recovery completion of 5-aminolevulinic acid.

The 5-aminolevulinic acid aqueous solution is produced in the above manner, and the 5-aminolevulinic acid hydrochloride can be produced by adding chloride ion to this aqueous solution. The amount of chloride ion to be added can be deduced from the amount of 5-aminolevulinic acid to be adsorbed by the cation exchange resin, and it is preferably from 1 to 100 times (molar ratio), more preferably from 1 to 10 times (molar ratio), based on the amount of 5-aminolevulinic acid to be desorbed from the cation exchange resin. In this connection, the desorbed amount of 5-aminolevulinic acid deduced from the adsorbed 5-aminolevulinic acid varies depending on the species and volume of the cation exchange resin, ammonia concentration of the desorption liquid, rate of liquid passing and the like, but recovery yield of 5-aminolevulinic acid is generally from 60 to 100%.

As the source of chloride ion, hydrochloric acid, potassium chloride, sodium chloride, ammonium chloride, zinc chloride, choline chloride, iron chloride and the like can be exemplified, which may be used as a combination of two or more thereof, and of which hydrochloric acid is particularly preferred. In addition, the chloride ion source can be used by dissolving in a solvent which can be used in carrying out the aforementioned adsorption of 5-aminolevulinic acid by the cation exchange resin. Preferred solvent is water. The method for adding chloride ion is not particularly limited.

It is possible to concentrate 5-aminolevulinic acid by repeating two or more times of the adsorption of this 5-aminolevulinic acid recovery aqueous solution by the cation exchange resin and subsequent desorption with cation-containing aqueous solution. 5-Aminolevulinic acid concentration of the 5-aminolevulinic acid recovery aqueous solution can be increased when adsorption ratio of 5-aminolevulinic acid to the column is high as its column adsorption condition, and when ion concentration of the desorption liquid is high as the desorption condition, so that it is possible to adjust 5-aminolevulinic acid concentration of the 5-aminolevulinic acid recovery aqueous solution in response to the purpose. In the case of repeating such an ion exchange column concentration step of 5-aminolevulinic acid two or more times, it is not particularly necessary to add chloride ion to the 5-aminolevulinic acid recovery aqueous solution and other acids may be used. Particularly, these acids may not be added when a hydrogen ion type cation exchange resin is used.

In this connection, the 5-aminolevulinic acid aqueous solution means the aqueous solution recovered in the aforementioned manner, and it also includes a concentrated aqueous solution, a diluted aqueous solution or a pH-adjusted aqueous solution in which its pH was adjusted with the aforementioned pH adjusting agent or the like.

The 5-aminolevulinic acid hydrochloride may be either a solid or a solution. The solution means a state in which it is dissolved or dispersed in a solvent including water. It also includes a pH-adjusted solution in which its pH was adjusted with the aforementioned pH adjusting agent or the like. In order to obtain 5-aminolevulinic acid hydrochloride as crystals, this is effected by carrying out addition of a poor solvent to the 5-aminolevulinic acid aqueous solution obtained by the aforementioned manner and the aqueous solution obtained by adding chloride ion.

As the poor solvent, it is not particularly limited with the proviso that it causes precipitation of crystals of 5-aminolevulinic acid hydrochloride, and its examples include alcohols (methanol, ethanol, normal propanol, isopropanol, normal butanol, isobutanol and the like), ethers (diethyl ether, diisopropyl ether, dioxane, tetrahydrofuran, dimethoxyethane and the like), esters (methyl acetate, ethyl acetate, propyl acetate, isopropyl acetate, γ-butyrolactone and the like), ketones (acetone, methyl ethyl ketone and the like), nitrites (acetonitrile, benzonitrile and the like) and the like, of which alcohols or ketones are preferable, and methanol, ethanol, isopropanol, normal propanol or acetone is particularly preferable. Two or more of poor solvents may be used as a mixture, but ethanol, acetone or isopropanol is particularly preferable.

The temperature when the 5-aminolevulinic acid aqueous solution desorbed from the cation exchange resin is mixed with hydrochloric acid is preferably from −20 to 60° C. under such a condition that the mixture is not solidified. In response to the necessity, dehydration concentration may be carried out, or an evaporator can be used. In addition, it is desirable that collection of the precipitated 5-aminolevulinic acid hydrochloride crystals is carried out by filtration.

EXAMPLES

The following describes the invention further in detail based on examples, but the invention is not limited thereto.

Example 1

A 10 ml portion of a strong acid cation exchange resin (mfd. by Dow Chemical, Dowex-50) was packed in an empty column, and 2 M hydrochloric acid aqueous solution and 2 M ammonia aqueous solution were passed through the column to prepare an ammonium ion-bonded ion exchange column.

On the other hand, a glycine-coexisting 5-aminolevulinic acid culture (25 mM 5-aminolevulinic acid, 11 mM glycine) was prepared by the same method of JP-A-11-42083, and 4 samples adjusted to pH 2.0, pH 3.0, pH 4.0 and pH 5.0 with concentrated sulfuric acid were prepared therefrom. A 50 ml portion of each of these cultures was applied to the aforementioned ammonium ion type ion exchange column.

The liquid which passed through the ion exchange column was recovered, and adsorption characteristics of 5-aminolevulinic acid and glycine to the ion exchange column were observed by a thin layer chromatography. Regarding the conditions of thin layer chromatography, a silica gel thin layer plate was used as the solid phase, and a 70:30 mixture of ethanol and water as the mobile phase. After the development, ninhydrin was sprayed thereto, and the amino acids were detected. Results of this qualitative test are shown in Table 1.

TABLE 1

Amount of amino acids contained in the culture passed-through liquid in cation exchange column purification

| Fermentation liquid pH | Glycine | 5-Aminolevulinic acid |
|---|---|---|
| 2.0 | − | − |
| 3.0 | ± | − |
| 4.0 | ++ | − |
| 5.0 | ++ | + |

A glycine-containing 5-aminolevulinic acid fermentation liquid was passed through a strong acid cation exchange column of ammonium form, and the amount of amino acids in the liquid passed through the column was analyzed by a thin layer chromatography.
−: not found,
±: extremely little,
+: little,
++: significant (concentration corresponding to the cation exchange column inlet side culture)

Example 2

A 10 ml portion of a strong acid cation exchange resin (mfd, by Dow Chemical, Dowex-50) was packed in an empty column, and 2 M hydrochloric acid aqueous solution and 2 M ammonia aqueous solution were passed through the column to prepare ion exchange column of ammonium form.

On the other hand, a 5-aminolevulinic acid culture containing glycine as an impurity (25 mM 5-aminolevulinic acid, 6.7 mM glycine) was prepared by the same method of JP-A-11-42083, and 7 samples adjusted to pH 2.0, pH 3.0, pH 4.0, pH 4.4, pH 4.6, pH 4.8 and pH 5.0 with concentrated sulfuric acid were prepared therefrom. A 50 ml portion of each of these cultures was applied to the aforementioned ion exchange column of ammonium form. The liquid which passed through the column was recovered, and adsorption ratio of 5-aminolevulinic acid was measured. As the results shown in Table 2, 5-aminolevulinic acid adsorbed efficiently to the ion exchange column of ammonium form under such a condition that the aqueous solution of 5-aminolevulinic acid was set to pH 4.0 or lower.

TABLE 2

Adsorption ratio of 5-aminolevulinic acid to the column in cation exchange column purification

| Fermentation liquid pH | Adsorption ratio (%) of 5-aminolevulinic acid |
|---|---|
| 2.0 | 100 |
| 3.0 | 100 |
| 4.0 | 100 |
| 4.4 | 95.6 |
| 4.6 | 86.7 |
| 4.8 | 68.0 |
| 5.0 | 64.0 |

A glycine-containing 5-aminolevulinic acid culture was passed through a strong acid cation exchange column of ammonium form, and the concentration of 5-aminolevulinic acid in the culture and the liquid passed through the column was measured to calculate the adsorption ratio.

Example 3

10 ml portion of a strong acid cation exchange resin (mfd, by Organo, Amberlite IR-120B) was packed in an empty column, and 2 M hydrochloric acid aqueous solution and 2 M ammonia aqueous solution were passed through the column to prepare ion exchange column of ammonium form.

On the other hand, a 5-amino levulinic acid culture (25 mM 5-aminolevulinic acid, 6.7 mM glycine) was prepared by the same method of JP-A-11-42083, and 3 samples adjusted to pH 3.0, pH 3.5 and pH 4.0 with concentrated sulfuric acid were prepared therefrom. A 100 ml portion of each of these cultures was applied to the aforementioned ion exchange column of ammonium form, and then 100 ml of ion exchange water was passed through the column. While carrying out this operation, the liquid which passed through the column was recovered by every 1 column volume to measure the 5-aminolevulinic acid concentration. The results of this are shown in FIG. 1.

Figure 2:
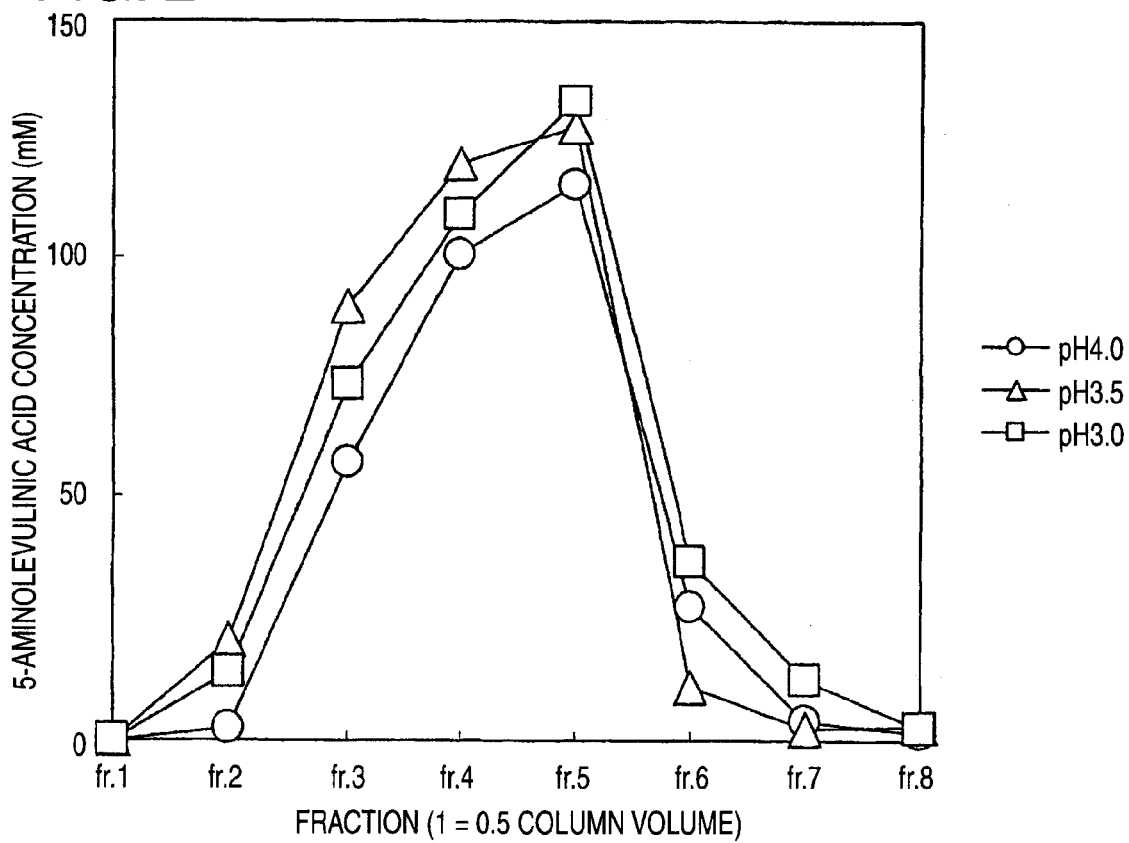
FIG. 2 is a graph showing a relationship between the pH of a crude aqueous solution containing 5-aminolevulinic acid and the 5-aminolevulinic acid concentration of a column passed-through liquid in column desorption of 5-aminolevulinic acid.

Subsequently, the 5-aminolevulinic acid adsorbed by the column was desorbed using 0.3 M ammonia aqueous solution. While carrying out this operation, the liquid which passed through the column was recovered by every 0.5 column volume to measure the 5-aminolevulinic acid concentration. The results of this are shown in FIG. 2. All of the obtained fractions were analyzed by the thin layer chromatography described in Example 1, but glycine was not detected.

The above results are summarized in Table 3 as the recovery yield of 5-aminolevulinic acid. As a result, it was able to purify and concentrate 5-aminolevulinic acid using the ion exchange column, within a 5-aminolevulinic acid culture pH range of from 3.0 to 4.0, so that the 5-aminolevulinic acid aqueous solution was obtained.

The above results are summarized in Table 3 as the recovery yield of 5-aminolevulinic acid. As a result, it was able to purify and concentrate 5-aminolevulinic acid using the ion exchange column, within a 5-aminolevulinic acid culture pH range of from 3.0 to 4.0, so that the 5-aminolevulinic acid aqueous solution was obtained.

TABLE 3

Influence on the ion exchange efficiency by the difference in pH of culture

| Fermentation liquid pH | Amount of 5-aminolevulinic acid adsorbed by the column (mg) | Amount of 5-aminolevulinic acid desorbed from the column (mg) | Recovery yield (%) |
|---|---|---|---|
| 3.0 | 246 | 246 | 100 |
| 3.5 | 242 | 243 | 100 |
| 4.0 | 207 | 202 | 98.0 |

Example 4

A 10 ml portion of a strong acid cation exchange resin (mfd, by Organo, Amberlite IR-120B) was packed in an empty column, and 2 M hydrochloric acid aqueous solution and 2 M ammonia aqueous solution were passed through the column to prepare ion exchange column of ammonium form.

On the other hand, a glycine-coexisting 5-aminolevulinic acid culture (27 mM 5-aminolevulinic acid, 20 mM glycine) was prepared by the same method of JP-A-11-42083, and 2 samples adjusted to pH 3.5 or pH 4.0 with concentrated sulfuric acid were prepared therefrom. A 160 ml portion of each of these cultures was applied to the aforementioned ion exchange column of ammonium form.

Figure 3:
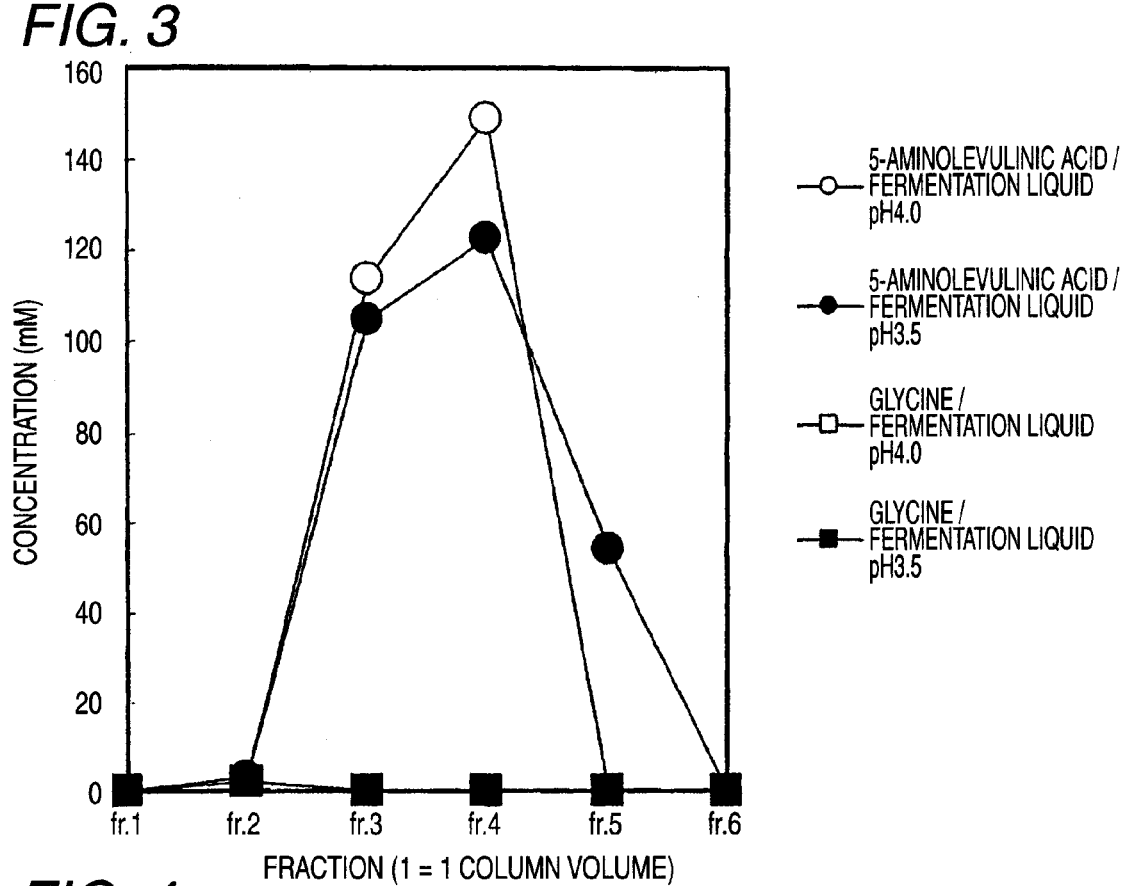
FIG. 3 is a graph showing a relationship between the 5-aminolevulinic acid concentration and the glycine concentration of a column eluate in desorption of 5-aminolevulinic acid.

Subsequently, the 5-aminolevulinic acid adsorbed by the column was desorbed using 0.3 M ammonia aqueous solution. While carrying out this operation, the liquid which passed through the column was recovered by every 1 column volume to measure the concentration of 5-aminolevulinic acid and glycine. The results of this are shown in FIG. 3. The 20 mM of glycine which was contained in the culture was not observed in the 5-aminolevulinic acid recovery liquid after the ion exchange column purification.

Example 5

A 170 ml portion of a strong acid cation exchange resin (mfd, by Organo, Amberlite IR-120B) was packed in an empty column, and 2 M hydrochloric acid aqueous solution was passed through the column to prepare ion exchange column of hydrogen form.

On the other hand, a 5-aminolevulinic acid aqueous solution was prepared from a 5-aminolevulinic acid culture by the same method of Example 3 and adjusted to pH 4.0 by adding concentrated sulfuric acid. A 2000 ml portion of this 5-aminolevulinic acid aqueous solution (109 mM 5-aminolevulinic acid) was applied to the aforementioned cation exchange column of hydrogen form, and then ion exchange water was passed through the column.

Figure 4:
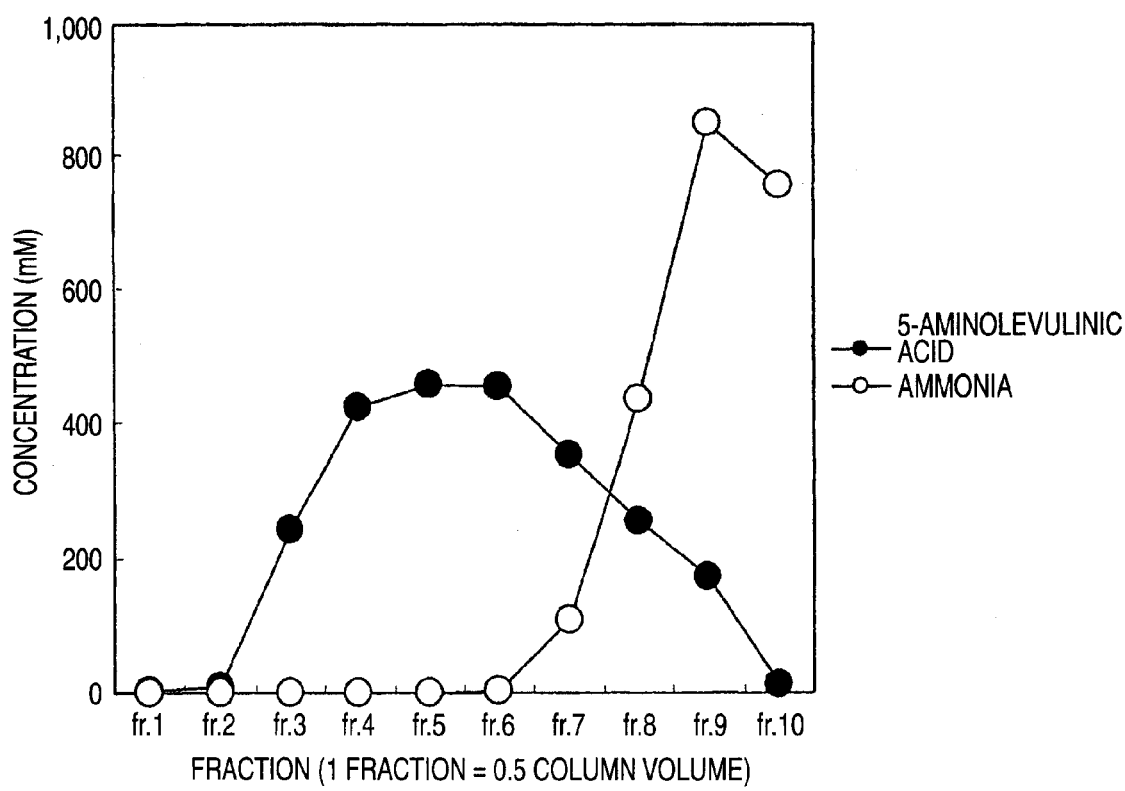
FIG. 4 is a graph showing a relationship between the 5-aminolevulinic acid concentration and the ammonia concentration of a column eluate in desorption of 5-aminolevulinic acid.

Subsequently, the 5-aminolevulinic acid adsorbed by the column was desorbed using 1 M ammonia aqueous solution. While carrying out this operation, the liquid which passed through the column was recovered by every 0.5 column volume to measure the concentration of 5-aminolevulinic acid and ammonia. The results of this are shown in FIG. 4. The concentration of 5-aminolevulinic acid increased along with the pass-through of the 1 M ammonia aqueous solution, and 5-aminolevulinic acid was concentrated to a concentration of 460 mM when the pass-through of 1 M ammonia aqueous solution reached around 2.5 column volumes. At this period of time, contamination of ammonium ion as an impurity was 1 mM or less. Thereafter, the concentration of ammonia increased accompanied by the completion of desorption of 5-amino levulinic acid.

Example 6

A 10 ml portion of a strong acid cation exchange resin (mfd, by Organo, Amberlite IR-120B) was packed in an empty column, and 2 M hydrochloric acid aqueous solution was passed through the column to prepare ion exchange column of hydrogen form.

On the other hand, a 5-aminolevulinic acid aqueous solution (pH 6.6) was prepared from a 5-aminolevulinic acid culture by the same method of Example 3. This aqueous solution was divided into two, and one of them was adjusted to pH 3.2 by adding concentrated sulfuric acid. A 130 ml portion of each of these 5-aminolevulinic acid aqueous solutions (92 mM 5-aminolevulinic acid) was applied to the aforementioned cation exchange column of hydrogen form, and then ion exchange water was passed through the column. Subsequently, the 5-aminolevulinic acid adsorbed by the column was desorbed using 0.5 M ammonia aqueous solution.

These results are shown in Table 4. Regarding the 5-aminolevulinic acid aqueous solutions of pH 6.6 and pH 3.2, 5-aminolevulinic acid was not detected in the liquid which passed through the column in the column adsorption step in both cases, thus showing that 5-aminolevulinic acid was efficiently adsorbed. In addition, recovery yield of 5-aminolevulinic acid was from 98.0 to 99.1%.

TABLE 4

Influence on the ion exchange efficiency by the difference in pH of 5-aminolevulinic acid aqueous solution

| 5-Aminolevulinic acid aqueous solution pH | 5-aminolevulinic acid adsorbed by the column (mg) | 5-aminolevulinic acid desorbed from the column (mg) | Recovery yield (%) |
|---|---|---|---|
| 3.2 | 1,563 | 1,549 | 99.1 |
| 6.6 (no pH adjustment) | 1,563 | 1,532 | 98.0 |

Example 7

A 50 liter portion of a strong acid cation exchange resin (mfd, by Mitsubishi Kagaku, SK-1B(H)) was packed in an empty column, and 2 M hydrochloric acid aqueous solution and 2 M ammonia aqueous solution were passed through the column to prepare an ammonium ion-bonded ion exchange column.

Figure 5:
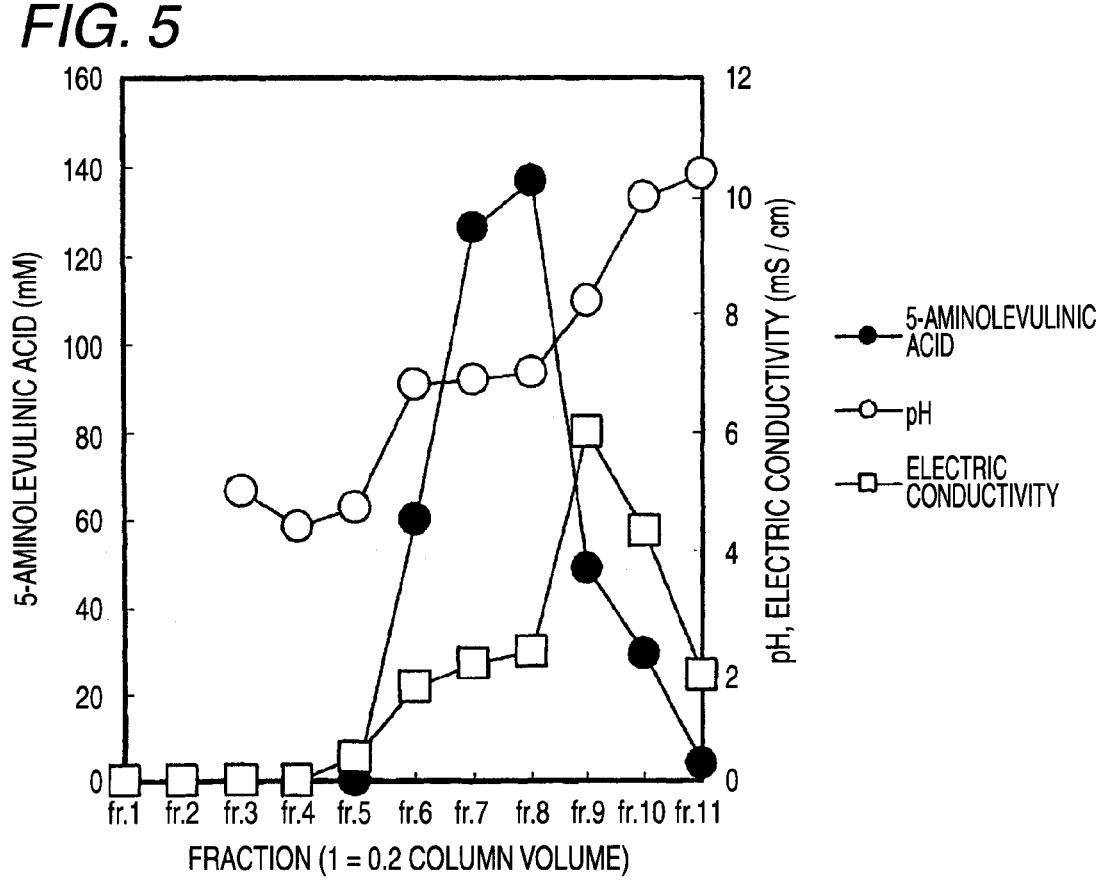
FIG. 5 is a graph showing a relationship between the 5-aminolevulinic acid concentration and the electric conductivity or pH of a column eluate in desorption of 5-aminolevulinic acid.
Figure 6:
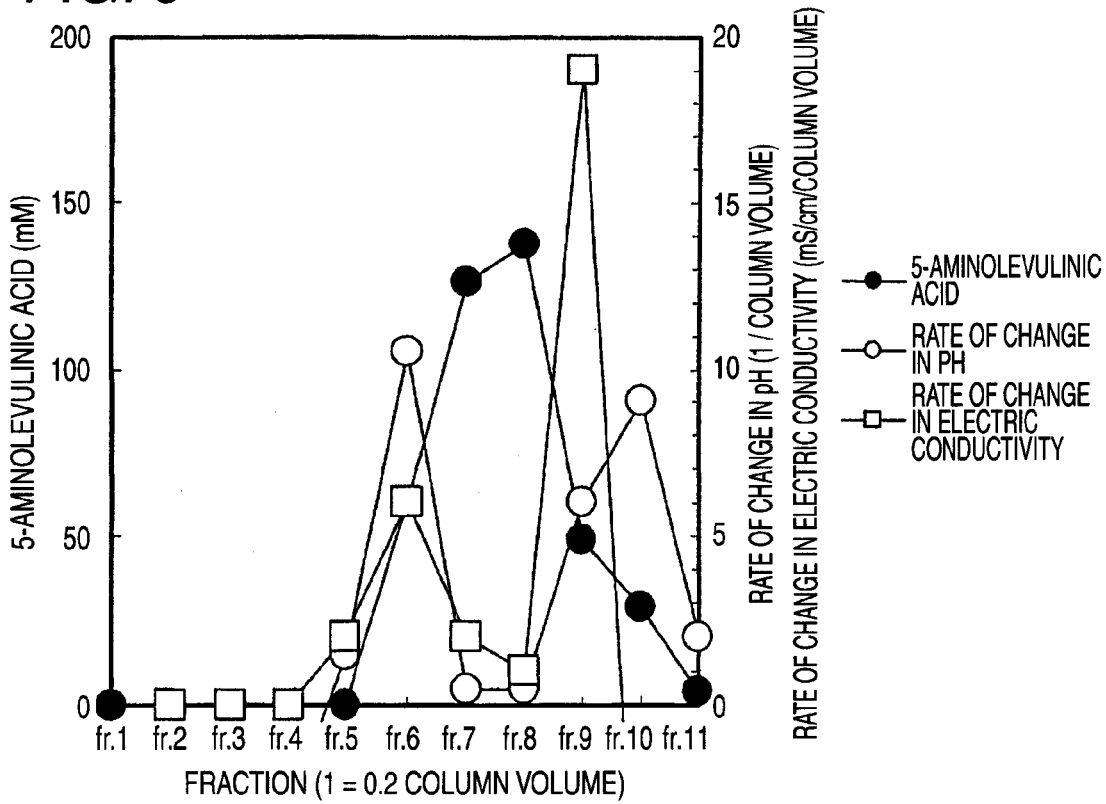
FIG. 6 is a graph showing a relationship between the 5-aminolevulinic acid concentration of a column eluate and the rate of change in electric conductivity or rate of change in pH of a column eluate in desorption of 5-aminolevulinic acid. The rate of change in electric conductivity or rate of change in pH in this case was expressed as a rate of change per column volume.

On the other hand, a 5-aminolevulinic acid fermentation liquid (24 mM 5-aminolevulinic acid) was prepared by the same method of JP-A-11-42083, and adjusted to pH 4.0 with concentrated sulfuric acid. A 280 liter portion of this culture was applied to the aforementioned ion exchange column of ammonium form, and then 100 ml of ion exchange water was passed through it. Subsequently, the 5-aminolevulinic acid adsorbed by the column was desorbed using 0.3 M ammonia aqueous solution. While carrying out this operation, the liquid which passed through the column was recovered by every 0.2 column volume to measure 5-aminolevulinic acid concentration, electric conductivity and pH. As these results shown in FIG. 5, the electric conductivity increased and the pH also increased to about 6.8 at the time of starting desorption of 5-aminolevulinic acid. Thereafter, the 5-aminolevulinic acid concentration increased, but the electric conductivity and pH showed no significant changes. In addition, the electric conductivity rapidly increased and the pH also increased rapidly at the time of the completion of desorption of 5-amino levulinic acid. These changes are shown in FIG. 6 as the rates of changes.

Example 8

A 5-aminolevulinic acid aqueous solution was prepared by the same method of Example 5, and 2 times volume, based on the amount of 5-aminolevulinic acid, (molar ratio) of hydrochloric acid was added thereto. Subsequently, this was concentrated using an evaporator to prepare a 5-aminolevulinic acid hydrochloride aqueous solution (3 M 5-aminolevulinic acid). The 5-aminolevulinic acid hydrochloride solution was added dropwise to the poor solvents described in Table 5, and the thus precipitated crystals of 5-aminolevulinic acid hydrochloride were recovered on a filter paper to measure their weights after air-drying.

TABLE 5

Crystallization of 5-aminolevulinic acid hydrochloride by poor solvents

| Poor solvent | Ethanol | Acetone | Normal propanol |
|---|---|---|---|
| Mixed volume* | 6 ml:20 ml | 2 ml:20 ml | 2 ml:20 ml |
| Precipitated crystals (g) | 0.12 | 1.03 | 0.43 |
| Purity (%) | 98.4 | 99.5 | 98.5 |

*Mixed volume of 5-aminolevulinic acid aqueous solution and organic solvent

Example 9

A 140 ml portion of a strong acid cation exchange resin (mfd, by Mitsubishi Kagaku, SK-1B(H)) was packed in an empty column, and 1 M ammonium chloride aqueous solution was passed through the column to prepare ion exchange column of ammonium form.

On the other hand, a 5-aminolevulinic acid culture (60 mM 5-aminolevulinic acid) was prepared by the same method of JP-A-11-42083 and adjusted to pH 3.5 by adding concentrated sulfuric acid thereto. A 280 ml portion of this culture was applied to the aforementioned ion exchange column of ammonium form, and then the column was washed by passing ion exchange water through it. Subsequently, the 5-aminolevulinic acid adsorbed by the column was desorbed using 0.3 M ammonia aqueous solution. By measuring electric conductivity and pH of the liquid which passed through the column, recovery of the passed-through liquid was started at the time when the electric conductivity increased from 0.0 mS/cm of the steady state to 1.0 mS/cm. This was 1.0 mS/cm/column volume as the rate of change in electric conductivity. In addition, recovery of the passed-through liquid was completed at the time when the pH reached pH 9.2 from pH 5.5 of the steady state. This was 3.7/column volume as the rate of change in pH. This recovered liquid was mixed with concentrated hydrochloric acid in an amount equivalent to that of 5-aminolevulinic acid (molar ratio). This recovered liquid was 390 ml, its 5-aminolevulinic acid hydrochloride concentration was 42 mM and its pH was 3.7.

A 20 ml portion of the strong acid cation exchange resin (mfd, by Mitsubishi Kagaku, SK-1B(H)) was packed in an empty column, and 1 M hydrochloric acid aqueous solution was passed through the column to prepare ion exchange column of hydrogen form. Next, the aforementioned recovery liquid of the liquid which passed through the column (5-aminolevulinic acid aqueous solution) was applied to the aforementioned ion exchange column of hydrogen form. Subsequently, the 5-aminolevulinic acid adsorbed by the column was desorbed using 0.5 M ammonia aqueous solution. By measuring electric conductivity and pH of the liquid which passed through the column, recovery of the passed-through liquid was started at the time when the electric conductivity increased from 0.0 mS/cm of the steady state to 1.0 mS/cm. This was 1.0 mS/cm/column volume as the rate of change in electric conductivity. In addition, recovery of the passed-through liquid was completed at the time when the pH reached pH 7.0 from pH 4.5 of the steady state. This was 2.5/column volume as the rate of change in pH. This recovered liquid (269 mM 5-aminolevulinic acid, 42 ml) was adjusted to pH 0.8 by adding concentrated hydrochloric acid.

This aqueous solution of 5-aminolevulinic acid hydrochloride was mixed with 0.5 g of activated carbon and stirred for 30 minutes. After removing the activated carbon powder by a membrane filtration, the aqueous solution of 5-aminolevulinic acid hydrochloride was dehydration-concentrated using an evaporator until its volume became 1 ml. 5-Aminolevulinic acid hydrochloride was crystallized by mixing this 5-aminolevulinic acid concentration liquid with 20 ml of isopropanol and then dried in vacuo. Finally, 1.47 g of 5-aminolevulinic acid hydrochloride was obtained, and its purity was 99.2%.

As in the above, 390 ml of a 5-aminolevulinic acid aqueous solution was obtained in the first stage ion exchange column step, but 389 ml of dehydration was necessary when an evaporator was used in dehydration-concentrating this 5-aminolevulinic acid aqueous solution to 1 ml. However, as a result of repeating the ion exchange column step again, it was able to concentrate the 5-aminolevulinic acid aqueous solution to 42 ml by 348 ml of dehydration. As this result, the dehydration volume required for the evaporator was reduced to 41 ml.

While the invention has been describe in detail and with reference to specific embodiments thereof, it will be apparent to one skilled in the art that various changes and modifications can be made therein without departing from the spirit and scope of the invention.

This application is based on a Japanese patent application filed on Sep. 21, 2005 (Japanese Patent Application No. 2005-273398), the contents thereof being thereby incorporated by reference. All of the cited references incorporated as the contents.

INDUSTRIAL APPLICABILITY

According to the invention, high purity 5-aminolevulinic acid aqueous solution and 5-aminolevulinic acid hydrochloride can be produced.

The invention claimed is:

1. A method for producing a 5-aminolevulinic acid aqueous solution, comprising the steps of:
   adjusting the pH of the crude solution comprising 5-aminolevulinic acid to a pH of about 2.5 to about 5.0;
   contacting the crude solution with a strong acid, ammonium ion-binding cation exchange resin, wherein the 5-aminolevulinic acid is adsorbed to the cation exchange resin;
   eluting the 5-aminolevulinic acid from the cation exchange resin with an aqueous solution containing a cation to obtain an eluate; and
   recovering the 5-aminolevulinic acid using a change in electric conductivity or pH of the eluate as an index.

2. A method for producing 5-aminolevulinic acid hydrochloride, comprising contacting the eluted aqueous solution of 5-aminolevulinic acid obtained by the method of claim 1 with chloride ions.

3. A method for producing crystals of 5-aminolevulinic acid hydrochloride, comprising the steps of:
   contacting the eluted aqueous solution of 5-aminolevulinic acid obtained by the method of claim 1 with chloride ions, and
   mixing the thus obtained solution with an organic solvent comprising an alcohol or ketone.

4. The method according to claim 3, wherein the organic solvent comprises methanol, ethanol, isopropanol, normal propanol or acetone.

5. The method for producing a 5-aminolevulinic acid aqueous solution according to claim 1, wherein the adsorption of 5-aminolevulinic acid from the crude 5-aminolevulinic acid solution onto the cation exchange resin, and the elution of the 5-aminolevulinic acid from the cation exchange resin with an aqueous solution containing a cation is repeated two or more times.

6. The method for producing a 5-aminolevulinic acid aqueous solution according to claim 1, wherein the cation is ammonium ion.

7. A method for producing 5-aminolevulinic acid hydrochloride, from a crude solution comprising the steps of:
   adjusting the pH of a crude solution comprising 5-aminolevulinic acid to a pH of about 2.5 to about 5.0;
   contacting the crude with a strong acid, ammonium ion-binding cation exchange resin, wherein the 5-aminolevulinic acid is adsorbed to the cation exchange resin;
   eluting the 5-aminolevulinic acid from the cation exchange resin with an aqueous solution containing a cation;

contacting the eluted aqueous solution of purified 5-aminolevulinic acid with chloride ions; and recovering the 5-aminolevulinic acid using a change in electric conductivity or pH of the eluate as an index.

8. The method for producing a 5-aminolevulinic acid hydrochloride according to claim 7, wherein the adsorption of 5-aminolevulinic acid from the crude 5-aminolevulinic acid solution onto the cation exchange resin, and the elution of the 5-aminolevulinic acid from the cation exchange resin with a solution containing a cation, is repeated two or more times.

9. The method for producing a 5-aminolevulinic acid hydrochloride according to claim 8, wherein a change in electric conductivity or pH of the eluate, in a respective value of 0.5 mS/cm or more or pH 0.5 or more per 1 column volume, is used as the index of recovery commencement, and a respective value of 2.5 mS/cm or more or pH 1 or more per 1 column volume is used as the index of recovery completion.

10. The method for producing a 5-aminolevulinic acid aqueous solution according to claim 1, wherein a change in electric conductivity or pH of the eluate, in a respective value of 0.5 mS/cm or more or a pH of 0.5 or more per 1 column volume, is used as the index of recovery commencement, and a respective value of 2.5 mS/cm or more or a pH of 1 or more per 1 column volume is used as the index of recovery completion.

11. The method for producing 5-aminolevulinic acid hydrochloride according to claim 2, wherein a change in electric conductivity or pH of the eluate, in a respective value of 0.5 mS/cm or more or a pH of 0.5 or more per 1 column volume, is used as the index of recovery commencement, and a respective value of 2.5 mS/cm or more or a pH of 1 or more per 1 column volume is used as the index of recovery completion.

12. The method or producing crystals of 5-aminolevulinic acid hydrochloride according to claim 3, wherein a change in electric conductivity or pH of the eluate, in a respective value of 0.5 mS/cm or more or a pH of 0.5 or more per 1 column volume, is used as the index of recovery commencement, and a respective value of 2.5 mS/cm or more or a pH of 1 or more per 1 column volume is used as the index of recovery completion.

13. The method for producing 5-aminolevulinic acid hydrochloride, from a crude solution, according to claim 7, wherein a change in electric conductivity or pH of the eluate, in a respective value of 0.5 mS/cm or more or a pH of 0.5 or more per 1 column volume, is used as the index of recovery commencement, and a respective value of 2.5 mS/cm or more or a pH of 1 or more per 1 column volume is used as the index of recovery completion.

\* \* \* \* \*